US00PP28484P2

(12) United States Plant Patent
Heemskerk

(10) Patent No.: US PP28,484 P2
(45) Date of Patent: Oct. 3, 2017

(54) ***HEMEROCALLIS* PLANT NAMED 'VER00157'**

(50) Latin Name: ***Hemerocallis* hybrid**
Varietal Denomination: VER00157

(71) Applicant: Gerardus J. C. M. Heemskerk, Noordwijk (NL)

(72) Inventor: Gerardus J. C. M. Heemskerk, Noordwijk (NL)

(73) Assignee: HEEMSKERK VASTE PLANTEN BV, Noordwijk (NL)

( * ) Notice: Subject to any disclaimer, the term of this patent is extended or adjusted under 35 U.S.C. 154(b) by 126 days.

(21) Appl. No.: 14/756,936

(22) Filed: Oct. 30, 2015

(51) Int. Cl.
*A01H 5/02* (2006.01)

(52) U.S. Cl.
USPC ..... Plt./312

(58) Field of Classification Search
USPC ..... Plt./263.1, 312
See application file for complete search history.

*Primary Examiner* — Susan McCormick Ewoldt
*Assistant Examiner* — Karen Redden
(74) *Attorney, Agent, or Firm* — Penny J. Aguirre

(57) ABSTRACT

A new cultivar of *Hemerocallis* named 'VER00157' that is characterized by its flowers that are orange-pink in color with yellow-green throats, its everblooming habit; blooming from June to October in The Netherlands, and its compact and dormant plant habit.

2 Drawing Sheets

Botanical classification: *Hemerocallis* hybrid.
Cultivar designation: 'VER00157'.

BACKGROUND OF THE INVENTION

The present invention relates to a new and distinct cultivar of *Hemerocallis* plant of hybrid origin, botanically known as *Hemerocallis* 'VER00157' and will be referred to hereafter by its cultivar name, 'VER00157'.

The new cultivar was developed through an on-going breeding program conducted by the Inventor in Noordwijk, The Netherlands. The objectives of the breeding program are to develop new cultivars of *Hemerocallis* that are everblooming with compact plant habits in a range of flower colors.

The new cultivar arose from crosses made in summer of 2006. Proprietary seed parent lines were pollinated with a mixture of pollen collected from proprietary pollen parents and the collected seeds were pooled and sown for evaluation. 'VER00157' was selected as a single unique plant from the resulting seedlings in summer of 2009. The specific parents are unknown and none of the possible parent plants are named or patented.

Asexual propagation of the new cultivar was first accomplished by division in Noordwijk, The Netherlands in 2009 by the Inventor. Asexual propagation by division and tissue culture has determined that the characteristics of this cultivar are stable and are reproduced true to type in successive generations.

SUMMARY OF THE INVENTION

The following traits have been repeatedly observed and represent the characteristics of 'VER00157'. These attributes in combination distinguish 'VER00157' as a new and distinct cultivar of *Hemerocallis*.

1. 'VER00157' exhibits flowers that are orange-pink in color with yellow-green throats.

2. 'VER00157' exhibits an everblooming habit; blooming from June to October in The Netherlands.
3. 'VER00157' exhibits a compact and dormant plant habit.

The new cultivar can be most closely compared to *Hemerocallis* cultivars 'VER00213' (U.S. Plant Pat. No. 26,605) and 'Avant Garde' (not patented). 'VER00213' is similar to 'VER00157' in having a compact and dormant plant habit and an extended flowering period. 'VER00213' differs from 'VER00157' in having lighter colored sepals (bi-colored flowers) and a trumpet shaped flower that opens less widely. 'Avant Garde' is similar to 'VER00157' in having flowers that are similar in color and in having a dormant plant habit. 'Avant Garde' differs from 'VER00157' in having a much larger flower, in lacking a continuously blooming habit, and in having broader leaves.

BRIEF DESCRIPTION OF THE DRAWINGS

The accompanying colored photographs illustrate the overall appearance and distinct characteristics of the new *Hemerocallis*. The photographs were taken of a 6 month-old plant of the new cultivar as field grown in Noordwijk, The Netherlands and place in a container for the photographs.

The photograph in FIG. 1 provides a side view of 'VER00157' in bloom and depicts its compact plant habit.

Figure 1:
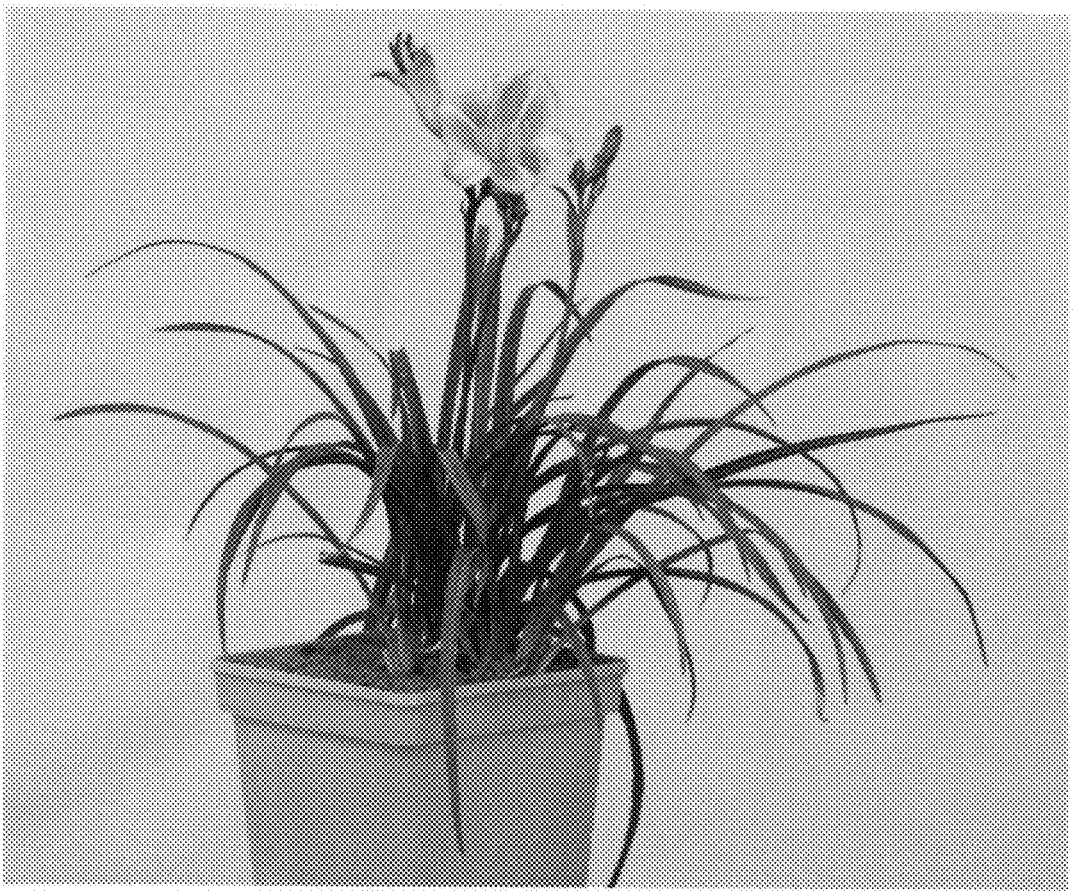
Figure 2:
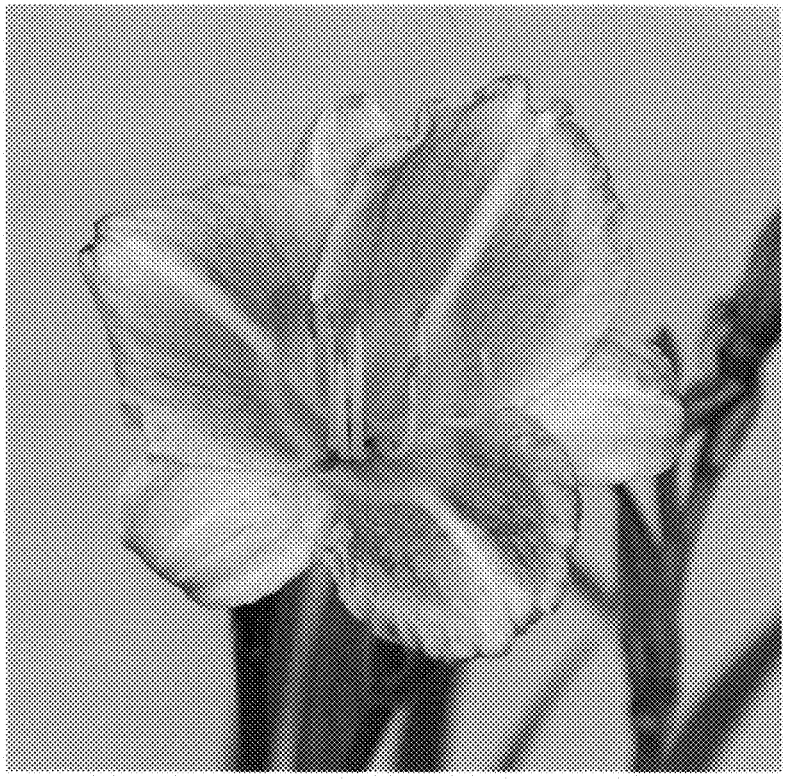

The photograph in FIG. 2 provides a close-up view of a flower of 'VER00157'.

Figure 3:
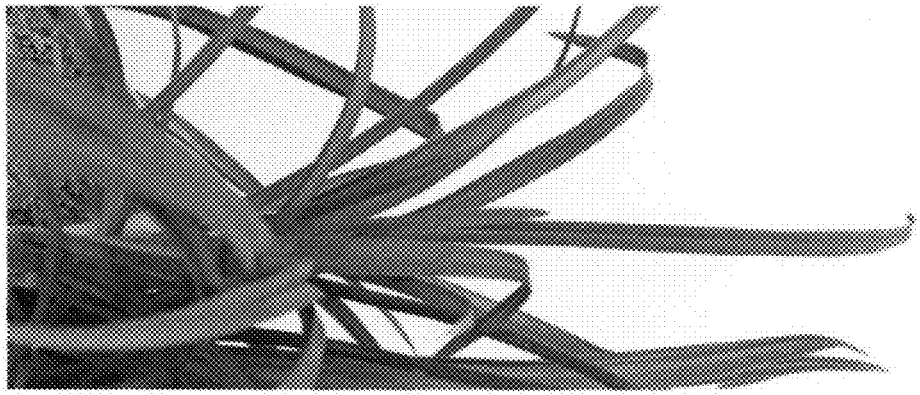

The photograph in FIG. 3 provides a close-up view of the foliage of 'VER00157'.

The colors in the photographs are as close as possible with the digital photography and printing techniques utilized and the color codes in the detailed botanical description accurately describe the new *Hemerocallis*.

DETAILED BOTANICAL DESCRIPTION OF THE PLANT

The following is a detailed description of 6 month-old plants of the new cultivar as field grown in Noordwijkerhout, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General characteristics:

*Blooming period*.—June to October in The Netherlands.

*Plant type*.—Herbaceous perennial.

*Plant habit*.—Compact, upright with arching leaves, dormant type.

*Height and spread*.—Reaches about 35 cm in height and 40 cm in spread (2 year-old plant in the landscape).

*Hardiness*.—At least in U.S.D.A. Zone 5.

*Diseases*.—No particular susceptibility or resistance has been observed.

*Root description*.—Fleshy with fibrous secondary roots.

*Propagation*.—Division and tissue culture.

*Growth rate*.—Moderate, 4 months to fully root a single fan division in a 18-cm container and 8 months to produce a No. 1 division in the field from a single fan.

Foliage description:

*Leaf shape*.—Linear, moderately carinate and curved.

*Leaf division*.—Simple.

*Leaf base*.—Decurrent.

*Leaf apex*.—Long acute with a short apiculate outer tip.

*Leaf venation*.—Parrallel, color upper surface; 137B, color lower surface; 137D.

*Leaf margins*.—Entire.

*Leaf attachment*.—Decurrent, no petioles.

*Leaf arrangement*.—Basal rosette.

*Leaf orientation*.—Held upright to pendulant.

*Leaf surface*.—Both surfaces glabrous, upper surface moderately glossy, lower surface matte.

*Leaf color*.—Young leaves upper surface; color between 143A and 144A (closest to 143A), young leaves lower surface; 143A, mature leaves upper and lower surface; 137B.

*Leaf size*.—Up to 39.8 cm in length, an average of 1.5 cm in width.

*Leaf quantity*.—Average of 8 per rosette.

Flower description:

*Inflorescence type*.—Scape bearing a panicle of single flowers.

*Inflorescence size*.—Varies with opening of flowers, an average of 12.8 cm in width and 12.3 cm in height.

*Lastingness of flowers*.—About 24 hours, self cleaning.

*Flower size*.—An average of 8.3 cm in length and 8 cm in diameter.

*Flower fragrance*.—None.

*Flower number*.—Average of 10.

*Flower aspect*.—Upright to outward.

*Flower bud*.—Oblong to narrow obovate in shape, average of 4.6 cm in length and 1.2 cm in width, color 151B, tinged with N144C to N144D, base N144C, top is 143B.

*Rate of flower opening*.—About 20% of flowers open at a time, about 4 weeks for all flowers to open per scape.

*Flower attachment*.—Petiolate.

*Petals*.—3, obovate in shape, average of 8 cm in length and 4 cm in width, margins entire, slightly undulate, moderately crinkled, apex retuse, base fused (lower 22.5%), color upper surface when opening; a blend of 170B, 171C and 173B, narrow axial stripe (main vein area) 159A, base 9B and tinged with N144A, tube 150B, color lower surface when opening; a blend of 20B and 164C and 164D, margin areas N170C, base 12A, tube N144A to N144B, color upper surface when fully open; a blend of 170B, 171C and 173B, narrow axial stripe (main vein area) 159A, base 9B and tinged with N144A, tube 150B, color lower surface when fully open; a blend of 20B, 164C and 164D, margin areas N170C, base 12A, tube N144A to N144B.

*Sepals*.—3, rotate in arrangement, average of 7.6 cm in length, 2.4 cm in width, narrowly obovate in shape, entire margins, base fused, acute apex, color upper surface young and mature; 174C and 179C, midsection 16B, base N144A, tube 150B, color lower surface young and mature; 17B to 17C and tinged with N144A, tip 143A, tube N144A to N144B.

*Calyx*.—Rotate in shape, average of 5.6 cm in length and 7.2 cm in diameter.

*Peduncles*.—Flattened in shape, glabrous surface, average of 30.7 in length and diameter at the widest point is 6 mm, diameter at the most narrow point is 4 mm, average of 85° to soil level (=0°), strong in strength and color is between 137A and 143A.

*Pedicels*.—Average of 1 cm in length and 0.3 mm in diameter, glabrous surface, round in shape, strong in strength, held at an average angle of 40° to the peduncle (=0°), color is 143B.

Reproductive organs:

*Gynoecium*.—Pistil; 1, average of 7.7 cm in length, style; 7.6 cm in length, 18A to 18B in color, stigma; crested, 11D in color, ovary; oblong in shape, 144A in color.

*Androecium*.—Stamens; 6, anthers; dorsifixed and narrow oblong in shape, 5 mm in length and N200A in color; filament; 3.8 cm in length, 13B in color, pollen; moderate to high in quantity and 17A in color.

*Fruit/seeds*.—None observed.

It is claimed:

1. A new and distinct cultivar of *Hemerocallis* plant named 'VER00157' as herein illustrated and described.

* * * * *